United States Patent
Richard et al.

(10) Patent No.: US 6,322,582 B1
(45) Date of Patent: *Nov. 27, 2001

(54) DEVICE FOR FIXING A SUTURE THREAD TO A SURGICAL NEEDLE

(75) Inventors: Francois Richard, Leves; Jacques Descoueit, Manou, both of (FR)

(73) Assignee: Ethicon, Inc., Somerville, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/564,046

(22) Filed: May 5, 2000

Related U.S. Application Data

(62) Division of application No. 09/257,321, filed on Feb. 25, 1999.

(51) Int. Cl.$^7$ .................................................. A61B 17/06
(52) U.S. Cl. ................................................................ 606/226
(58) Field of Search ..................................... 606/222, 223, 606/224, 225, 226, 227; 206/63.3; 163/1, 2, 5; 223/102

(56) References Cited

U.S. PATENT DOCUMENTS

| | | | |
|---|---|---|---|
| 2,728,343 | * 12/1955 | Everett | 606/226 |
| 3,910,282 | 10/1975 | Messer et al. | |
| 3,980,177 | * 9/1976 | McGregor | 206/63.3 |
| 4,680,823 | 7/1987 | Jeal . | |
| 5,230,352 | * 7/1993 | Putnam et al. | 128/898 |
| 5,350,373 | * 9/1994 | Colligan | 606/1 |

FOREIGN PATENT DOCUMENTS

| | | |
|---|---|---|
| 591994 A2 | 4/1994 | (EP) . |
| 455640 A | 8/1913 | (FR) . |
| 1101669 A | 1/1968 | (GB) . |

* cited by examiner

Primary Examiner—Henry J. Recla
Assistant Examiner—Vy Q. Bui
(74) Attorney, Agent, or Firm—Emil Richard Skula

(57) ABSTRACT

The device for fixing a thread (25) to a surgical needle (22) includes a bearing piece (2) and a punch (16). The bearing piece (2) has a housing (10) adapted to receive a needle (22) so as to immobilize it when the punch (16) comes into contact with the needle.

5 Claims, 2 Drawing Sheets

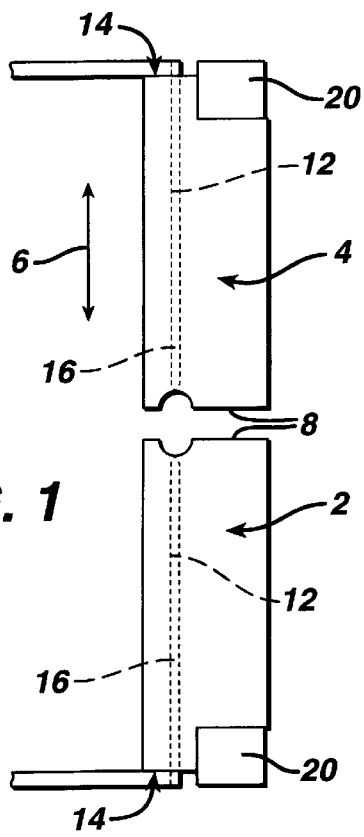
FIG. 1
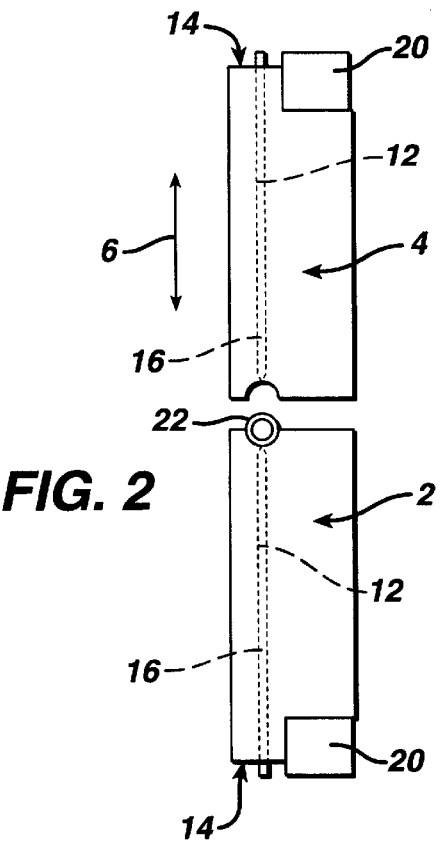
FIG. 2
FIG. 3
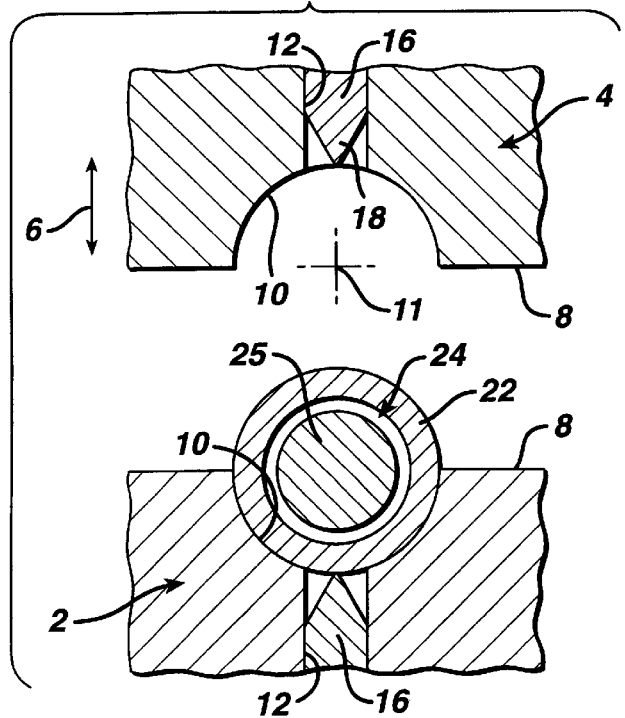
FIG. 8
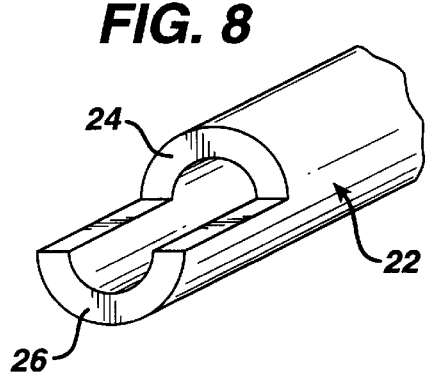

DEVICE FOR FIXING A SUTURE THREAD TO A SURGICAL NEEDLE

This appln. is a Div of Ser. No. 09/257,321 filed Feb. 25, 1999.

The invention relates to surgical needles receiving a suture thread.

Document U.S. Pat. No. 4,922,904 discloses a device for fixing a thread to a surgical needle. This device includes four punches which can move by sliding in the direction of one and the same point and are arranged in a cross formation. A needle, with a hollow end for receiving a thread which is to be fixed to the needle, is positioned at this point. The four punches then come simultaneously into contact with the needle so as to deform its wall, giving it a square cross-section, and thus crimp the thread in the needle.

However, this device has certain disadvantages. It requires a relatively large number of punching steps to guarantee effective fixing of the thread. It follows from this that it is necessary either to use a corresponding number of punches, something which takes up a lot of space and is expensive, or else to turn the needle between two punching steps, which leads to imprecise positioning under the different impacts. Moreover, this device alters the shape of the needle at the level of the punched section, in particular generating sharp edges.

It is an object of the invention to make available a device permitting a reduction in the number of punching steps needed for the needle, and preserving the general shape of the needle at the punching location.

With a view of achieving this object, the invention provides a device for fixing a thread to a surgical needle, including a bearing piece and a punch which is movable in the direction of the bearing piece, in which the bearing piece has a housing adapted to receive a needle so as to immobilize it when the punch comes into contact with the needle.

Thus, the point of impact of the punch on the needle is obtained with precision, and any sliding of the punch on the needle during impact is avoided. This results in much more effective punching with a view to fixing the thread to the needle. In particular, it is possible, without any danger of sliding, to use a punch with a conical end in order to bring a part of the wall of the needle into the thread. Moreover, the general shape of the needle is preserved. It is also possible to reduce the number of punching steps necessary for each needle in this way. This device additionally obviates the need to rotate the needle between two punching steps.

The device according to the invention will also be able to have one or more of the following characteristics:
- the punch is movable in the direction of the housing;
- the bearing piece is designed so that the needle rests by gravity in the housing;
- the bearing piece being a first bearing piece, the device includes a second bearing piece adapted so that the two bearing pieces immobilize the needle, in particular when the punch is not in contact with the needle;
- the housing being a first housing, the second bearing piece has a second housing adapted to receive the needle;
- the punch is movable through the second bearing piece;
- the punch is movable in the second housing;
- the punch being a first punch, the device includes a second punch which is movable through the bearing piece;
- the second punch is movable in the housing;
- the punch or at least one of the punches has an end of conical shape.

The invention also provides a method for fixing a thread to a surgical needle, in which method a needle receiving a thread is immobilized and the needle is punch, and in which the needle is immobilized in such a way that the position of a portion of the needle undergoing punching is predetermined.

This method can be implemented using the device according to the invention.

Advantageously, the needle is immobilized prior to the punching.

Advantageously, a portion of the needle undergoing punching is immobilized.

Advantageously, two zones of the needle are punched simultaneously.

Finally, the invention provides a surgical needle equipped with a thread fixed by means of the method according to the invention.

Other characteristics and advantages of the invention will also be evident from the following description of a preferred embodiment which is given as a non-limiting example. In the attached drawings;

FIG. 1 is an elevation view of a preferred embodiment of the device according to the invention;

FIG. 2 is a view of the device in FIG. 1 receiving a needle;

FIG. 3 is a view, on a larger scale, of a detail of the device in FIG. 2;

FIG. 8 is a view of the thread guide.

Figure 4:
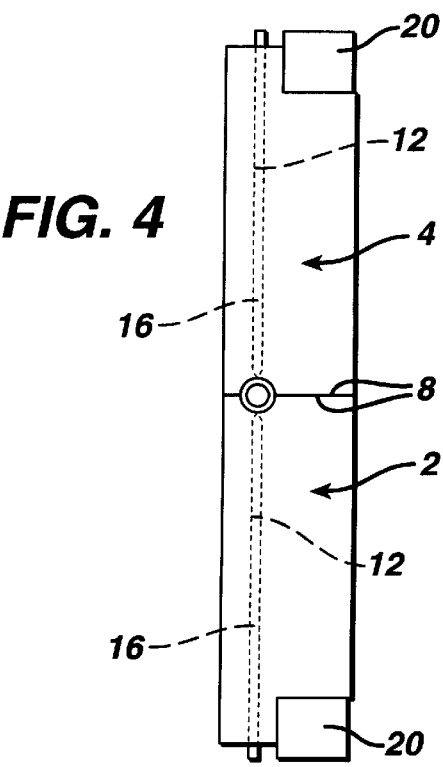
FIGS. 4, 5, 6 and 7 are views similar to FIGS. 2 and 3, showing two stages of the method according to the invention.

Referring to FIGS. 1, 2 and 3, in the preferred embodiment, the device according to the invention includes a lower bearing piece 2 integral with a frame (not shown) of the device, and an upper bearing piece 4 which can move by sliding in relation to the lower bearing piece 2, in the direction thereof, in a direction represented by the double arrow 6. The two bearing pieces 2, 4 have respective plane contact faces 8 which are perpendicular to the direction of displacement 6 and are adapted to come into surface contact with one another. The two bearing pieces 2, 4 have, in the area of the contact faces 8, respective housings 10 each formed by a recess or an indentation hollowed out in the contact face with a semi-circular cross-sectional profile and with a curved axis 11. The axis 11 extends in the plane of the associated contact face 8. The housings 10 are arranged in such a way that together they define a profiled enclosure of circular cross-section when the two bearing pieces 2, 4 are in mutual contact via their contact faces 8.

Each bearing piece 2, 4 has a rectilinear cylindrical conduit 12 extending in a direction parallel to the direction of displacement 6, from the housing 10 to an opposite face 14 of the bearing piece. Each conduit 12 thus opens out at both its ends. The axis of each conduit geometrically cuts the axis 11 of the associated housing 10. The two conduits 12 are in alignment with one another.

The device includes two punches 16 with a general cylindrical rectilinear shape, which can move by sliding in the respective conduits 12. Each punch 16 has an axial end 18 directed towards the other bearing piece 2, 4 and of conical shape, blunted at the point of the cone.

The device includes two return springs 20 associated with the respective punches 16 in such a way as to return the punch in the opposite direction to the associated housing 10. The device includes conventional means (not shown) for stressing each punch 16 counter to the associated spring 20 in the direction of the other bearing piece 2, 4.

The method of the invention can be implemented in the following way.

Use is made of a surgical suture needle 22 of a known type, having a tubular hollow axial end 24 of circular cross-section and opening out. Referring to FIGS. 2 and 3, the two bearing pieces 2, 4 being at a distance from one another, the needle 22 is placed in the housing 10 of the lower bearing piece 2. The needle rests by gravity in this housing and its position is determined, the device being designed so that the radius of the housing 10 corresponds to that of the needle 22.

The lower bearing piece 2 includes a thread guide 26 of semicylindrical shape designed such that in this position of the needle, the needle and the thread guide are coaxial, one end of the thread guide being contiguous with the hollow end of the needle. It is therefore easy to push a free end of a thread 25 into the hollow end of the needle. The thread can be single-stranded or braided, absorbable or nonabsorbable. It can be synthetic, natural or of plant origin.

Figure 5:
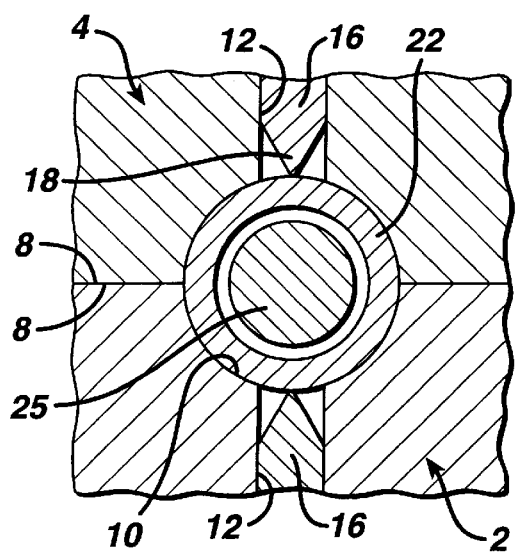

Referring to FIGS. 4 and 5, the upper bearing piece 4 is then lowered with its punch towards the lower bearing piece 2 in the direction 6 until the faces 8 come into contact with one another. The housings 10 thus define the complete indentation which encloses and immobilizes the needle, giving it a predetermined fixed position.

Figure 6:
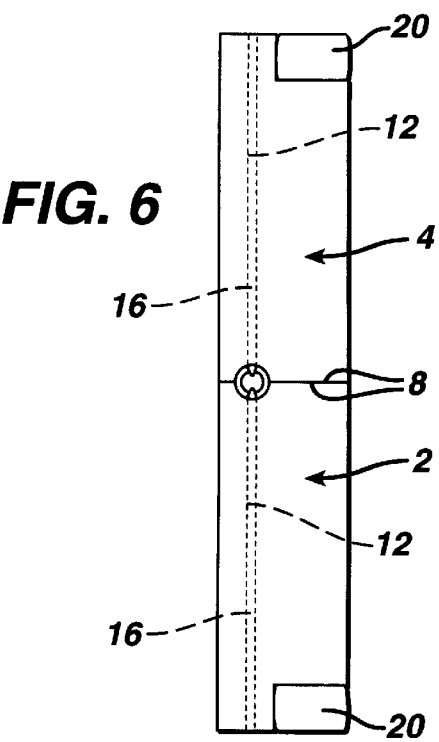
Figure 7:
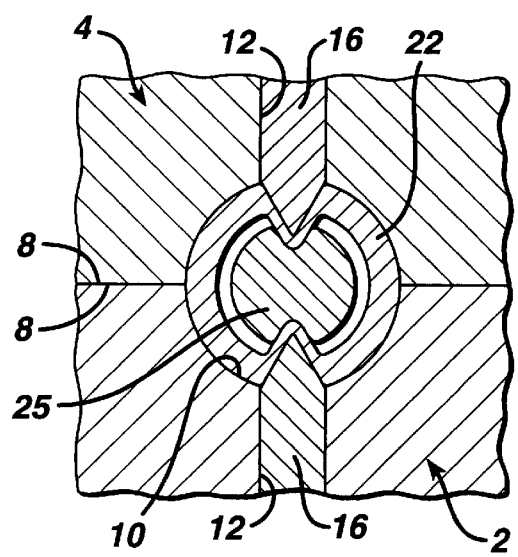

Referring to FIGS. 6 and 7, at the end of the travel of the upper bearing piece, the downward movement of the associated upper punch continues, and the lower punch is displaced upwards in the direction of the needle. Its hollow end is thus punched at two diametrically opposite points, where the wall of the needle is deformed inwards to form two internal projections between which the thread 25 is gripped.

Each punch 16 is then drawn back, after which the upper bearing piece 4 is lifted and the needle 22 is removed from the lower bearing piece. A needle is obtained on which the thread 25 is crimped effectively by a double punching.

The device allows the two punching steps to be performed exactly in the axis of the needle 22 and with the same penetration in the wall of the needle. By virtue of this device, the thread 25 can be fixed by means of two punching steps alone. The punched section of the needle retains its general circular shape. It is possible to dispense with rotating the needle between two punching steps.

Although less advantageous, it will be possible to omit the upper bearing piece 4 and/or the lower punch 16 by rotating the needle for a double punching.

What is claimed is:

1. A device for fixing a thread (25) to a surgical needle (22), comprising a bearing piece (2) and a punch (16) which is movable in the direction toward the bearing piece, characterized in that the bearing piece (2) has a first housing (10) adapted to complementally receive a needle (22) so as to immobilize it when the punch (16) is in contact with the needle, wherein the punch (16) is movable in the direction toward the first housing (10), wherein the bearing piece (2) is designed so that the needle rests by gravity in the first housing (10), wherein the device includes a second bearing piece (4) adapted so that the two bearing pieces (2, 4) immobilize the needle (22), when the punch (16) is not in contact with the needle, wherein the second bearing piece (4) has a second housing (10) adapted to complementally receive the needle, wherein the punch (16) is movable through the second bearing piece (4), and, wherein the punch (16) is movable into the second housing (10).

2. The device according to claim 1, characterized in that the punch (16) being a first punch, the device includes a second punch (16) which is movable through the bearing piece(2).

3. The device according to claim 1, characterized in that a second punch (16) is movable in the first housing (10).

4. The device according to claim 1, characterized in that the punch or at least one of the punches (16) has an end (18) of conic al shape.

5. A device for fixing a thread (25) to a surgical needle (22), comprising a bearing piece (2) and a punch (16) which is movable in the direction toward the bearing piece, characterized in that the bearing piece (2) has a first housing (10) adapted to complementally receive a needle (22) so as to immobilize it when the punch (16) is in contact with the needle, wherein the punch (16) is movable in the direction toward the first housing (10), wherein the bearing piece (2) is designed so that the needle rests by gravity in the first housing (10), wherein the device includes a second bearing piece (4) adapted so that the two bearing pieces (2, 4) immobilize the needle (22) when the punch (16) is not in contact with the needle, wherein the second bearing piece (4) has a second housing (10) adapted to complementally receive the needle, wherein the punch (16) is movable through the second bearing piece (4), wherein the punch (16) is movable into the second housing (10), and wherein the punch (16) is a first punch, and the device additionally comprises a second punch (16) which is movable through the bearing piece (2), and wherein the second punch (16) is movable in the first housing (10).

* * * * *